United States Patent
Chuchotiros et al.

(10) Patent No.: US 8,153,572 B2
(45) Date of Patent: Apr. 10, 2012

(54) CONDITIONING SHAMPOO COMPOSITION

(75) Inventors: Apirudee Chuchotiros, Changning District (CN); Colin Christopher David Giles, Changning District (CN); Anuchai Sinsawat, Changning District (CN)

(73) Assignee: Conopco, Inc., Englewood Cliffs, NJ (US)

( * ) Notice: Subject to any disclaimer, the term of this patent is extended or adjusted under 35 U.S.C. 154(b) by 0 days.

(21) Appl. No.: 12/920,469

(22) PCT Filed: Mar. 5, 2009

(86) PCT No.: PCT/EP2009/052598
§ 371 (c)(1),
(2), (4) Date: Oct. 28, 2010

(87) PCT Pub. No.: WO2009/112420
PCT Pub. Date: Sep. 17, 2009

(65) Prior Publication Data
US 2011/0053818 A1    Mar. 3, 2011

(30) Foreign Application Priority Data
Mar. 14, 2008 (EP) ................................. 08152752

(51) Int. Cl.
*A61K 8/04* (2006.01)
(52) U.S. Cl. ........ 510/119; 510/122; 510/507; 424/70.1
(58) Field of Classification Search .................. None
See application file for complete search history.

(56) References Cited

U.S. PATENT DOCUMENTS

| 4,390,033 A | 6/1983 | Khalil ........................... 132/202 |
| 5,034,218 A | 7/1991 | Duvel ............................. 424/70 |
| 5,093,112 A * | 3/1992 | Birtwistle et al. ......... 424/70.23 |
| 6,617,292 B2 | 9/2003 | Perron ........................... 510/119 |
| 2003/0223952 A1 | 12/2003 | Wells et al. ................ 424/70.17 |
| 2006/0154836 A1 | 7/2006 | Ashoke et al. ................ 510/122 |
| 2007/0110700 A1 | 5/2007 | Wells et al. ................ 424/70.21 |

FOREIGN PATENT DOCUMENTS

| JP | 2006 63044 | 9/2004 |
| JP | 2004 307463 | 11/2004 |
| WO | 03/047541 | 6/2003 |
| WO | 2005/039517 | 5/2005 |
| WO | 2008/063471 | 5/2008 |

OTHER PUBLICATIONS

PCT International Search Report in PCT application PCT/EP2009/052598.
PCT International Search Report in PCT application PCT/EP2007/061678.
European Search Report in EP application EP 06 12 3679.
Japanese Abstract—JP 2004 307463, published Nov. 4, 2004.
"*Aluminum oxide*", XP002433100, Wikipedia Encyclopedia (retrieved from Internet May 2007) pp. 1-4.
Co-pending Application: Applicant: Giles et al., U.S. Appl. No. 12/513,676, filed May 6, 2009.
Co-pending Application: Applicant: Giles et al., U.S. Appl. No. 12/513,677, filed May 6, 2009.

* cited by examiner

*Primary Examiner* — Necholus Ogden, Jr.
(74) *Attorney, Agent, or Firm* — Ronald A. Koatz

(57) ABSTRACT

Aqueous conditioning shampoo comprising cleansing surfactant and a conditioning gel network, the gel network comprising a particulate having a melting point above 70° C. and glyceryl monostearate.

1 Claim, No Drawings

CONDITIONING SHAMPOO COMPOSITION

The present invention relates to a conditioning shampoo composition with improved stability.

Compositions comprising gel networks are known in the art and include those structured oily phases which are structured by a crystalline material. Typically these gel networks are dispersed in an aqueous cleansing phase to provide a conditioning benefit in a cleansing composition, such as a shampoo. Typical of such a disclosure is WO 2007/040571 (P&G) which describes shampoo compositions comprise (a) from about 5% to about 50% of one or more detersive surfactants, by weight of the shampoo composition; (b) a dispersed gel network phase comprising, by weight of the shampoo composition, (i) at least about 0.05% of one or more fatty amphiphiles; (ii) at least about 0.01% of one or more secondary surfactants; and (iii) water; and (c) at least about 20% of an aqueous carrier, by weight of the shampoo composition.

Despite the prior art there remains a need for more stable conditioning shampoo compositions.

Accordingly, and in a first aspect, the present invention provides an aqueous conditioning shampoo comprising cleansing surfactant and a conditioning gel network, the gel network comprising a particulate having a melting point above 70° C. and glyceryl monostearate.

In a further aspect the present invention provides an aqueous conditioning shampoo comprising cleansing surfactant and a structured conditioning gel phase, the gel phase comprising a particulate having a melting point above 70° C. and glyceryl monostearate.

We have surprisingly found that conditioning gel phases or gel networks comprising a particulate are more stable in the presence of glyceryl monostearate.

Preferred particulates include those with a melting point of above 75° C.

Preferably, the particulate has a platelet morphology. Alternatively, the particulate is hydrophobic. Preferred particulates include hydrophobically modified clays. Alternatives include waxes.

The total amount of glyceryl monostearate is preferably from 0.01 to 20%, more preferably from 0.1 to 10%, and most preferably from 0.5 to 5% by weight of the total composition.

The gel network is formed by combining the components at a temperature above the melting point of glyceryl monostearate in the presence of water. In a preferred method of manufacture, the glyceryl monostearate is melted in water and the particulate material is then added. In a more preferred method of manufacture, a quaternary ammonium compound is also added, preferably after the particulate material. A dispersion of liquid crystalline phase droplets is typically produced. It will be realised that, in effect, the gel network has another component: water. In preferred embodiments, the gel network comprises an $L_\beta$ lamellar phase dispersion at 25° C.

When the gel network also comprises a quaternary ammonium compound, the particles also have a melting point higher than this component. Typically, the solid particles have an inorganic core, although they may be surface-modified with organic groups.

Preferably, the particles have a platelet morphology or are hydrophobic.

"Platelet morphology" should be understood to mean that the particles have a "plate-like" shape, i.e. their lengths in two orthogonal directions are considerably greater than their length in the third orthogonal direction. Typically, the particles have length and breadth that are each independently at least 10 times greater their depth; where "length", "breadth", and "depth" are expressions for the three orthogonal directions.

Suitable particles having platelet morphology are clays having a layered structure. Such clays may be anionic or cationic, i.e., they may have a net charge on the surface of the clay that is negative or positive, respectively.

Preferred particles having platelet morphology are anionic clays, such as smectite clays.

Typical smectite clays include the compounds having the general formula $Al_2(Si_2O_5)_2(OH)_2.nH_2O$ and the compounds having the general formula $Mg_3(Si_2O_5)_2(OH)_2.nH_2O$, and derivatives thereof, for example in which a proportion of the aluminium ions are replaced with magnesium ions or a proportion of the magnesium ions are replaced with lithium ions and/or some of the hydroxyl ions are replaced by fluoride ions; the derivatives may comprise a further metal ion to balance the overall charge.

Specific examples of suitable smectite clays are montmorillonites, volchonskoites, nontronites, saponites, beidelites and sauconites, particularly those having an alkali or alkaline earth metal ion within the crystal lattice structure. Preferred smectite clays are montmorillonites, nontronites, saponites, beidelites, sauconites and mixtures thereof. Particularly preferred are montmorillonites, e.g. bentonites and hectorites, with bentonites being especially preferred.

Particularly preferred particles having platelet morphology are hydrophobically-modified anionic clays; especially, hydrophobically-modified bentonite clay.

Hydrophobically-modified clays typically have organic cations replacing at least a proportion of the inorganic metal ions of the unmodified clay. Preferred organic cations for this purpose comprising one or more $C_6$-$C_{30}$ alkyl groups. The cationic group is preferably a quaternary ammonium group. Particularly preferred organic cations have two $C_6$-$C_{30}$ alkyl groups, for example:

distearyldimethylammonium;
dicetyldimethylammonium;
dimethyldi(hydrogenated tallow) ammonium;
dicetylmethylbenzylammonium;
dicocodimethylammonium;
dibehenyl/diarachidyldimethylammonium;
hydroxypropyl bis-stearylammonium;
dibehenyldimethylammonium;
dibehenylmethylbenzylammonium; and
dimyristyldimethylammonium.

Especially preferred particulate materials having platelet morphology are Quaternium-18 Bentonite, i.e. bentonite hydrophobically-modified by dimethyldi(hydrogenated tallow)ammonium cations) and Quaternium-90 Bentonite, an analogous material with two vegetable-derived fatty chains. Examples of such clays are Tixogel MP 100™ and Tixogel MP 100V™ from Sud Chemie. Other similar materials include Quaternium benzalkonium bentonite, Quaternium-18 hectorite, stearalkonium bentonite, stearalkonium hectorite and dihydrogenated tallow benzylmonium hectorite.

The particles having platelet morphology have a particle size such that preferably at least 50% and more preferably at least 80% of them are able to pass through a 90 micron screen, such as an air sieve as commonly used in the art.

The total amount of particles is preferably from 0.005 to 10%, more preferably from 0.01 to 5%, and most preferably from 0.01 to 1% by weight of the total composition.

The weight ratio of particles having platelet morphology to the fatty ester is preferably from 1:100 to 1:2, more preferably from 1:50 to 1:5, and most preferably from 1:30 to 1:10.

A quaternary ammonium compound having at least one carbon chain of length $C_{12}$-$C_{30}$ is a preferred component of the gel network. In preferred embodiments, the quaternary ammonium compound has only one carbon chain of length $C_{12}$-$C_{30}$. Typically, the one carbon chain of length $C_{12}$-$C_{30}$ is a linear (i.e. non-branched) hydrocarbon chain. Preferably, the one carbon chain of length $C_{12}$-$C_{30}$ is saturated. Preferably, the one carbon chain of length $C_{12}$-$C_{30}$ is of chain length $C_{12}$-$C_{22}$ and more preferably it is of chain length $C_{16}$-$C_{22}$. The one carbon chain of length $C_{12}$-$C_{30}$ is preferably of average chain length within four carbons, and more preferably within two carbon atoms, of the average chain length of the $C_{12}$-$C_{22}$ fatty alcohol also present in the gel network, in order to enhance the stability of the gel.

The quaternary ammonium compound having at least one carbon chain of length $C_{12}$-$C_{30}$ has three other carbon-containing substituents attached to the quaternary nitrogen atom. These are typically $C_1$-$C_4$ alkyl groups and are preferably methyl and/or ethyl groups; most preferably they are methyl groups.

Most preferably, the quaternary ammonium compound having at least one carbon chain of length $C_{12}$-$C_{30}$ is cetyltrimethylammonium chloride or benhenyltrimethylammonium chloride.

When present, the total amount of quaternary ammonium compound having at least one carbon chain of length $C_{12}$-$C_{30}$ is preferably from 0.005 to 10%, more preferably from 0.01 to 5%, and most preferably from 0.01 to 1% by weight of the total composition.

The weight ratio of quaternary ammonium compound having at least one carbon chain of length $C_{12}$-$C_{30}$ to particles having platelet morphology is preferably from 1:10 to 10:1, more preferably from 1:5 to 5:1, and most preferably from 1:2 to 2:1.

The molar ratio of quaternary ammonium compound having at least one carbon chain of length $C_{12}$-$C_{30}$ to glyceryl monostearate is preferably from 1:100 to 5:1, more preferably from 1:50 to 1:2, and most preferably from 1:30 to 1:10. These molar ratios apply particularly when the quaternary ammonium compound has only one carbon chain of length $C_{12}$-$C_{30}$.

The preferred viscosity for shampoo compositions according to the invention is from 3000 to 9000 cP (mPa·s), more preferably from 5000 to 7000 cP (mPa·s), and most preferably from 5500 to 6500 cP (mPa·s) at 30° C., as measured by a Brookfield viscometer equipped with a RVT pin number 5 at a measuring speed of 20 rpm.

Preferably, the composition will comprise at least 50%, preferably at least 60%, at most preferably at least 75% by weight of water.

Conditioning shampoo compositions according to the invention comprise one or more anionic cleansing surfactants, which are cosmetically acceptable and suitable for topical application to the hair.

Examples of suitable anionic cleansing surfactants are the alkyl sulphates, alkyl ether sulphates, alkaryl sulphonates, alkanoyl isethionates, alkyl succinates, alkyl sulphosuccinates, alkyl ether sulphosuccinates, N-alkyl sarcosinates, alkyl phosphates, alkyl ether phosphates, and alkyl ether carboxylic acids and salts thereof, especially their sodium, magnesium, ammonium and mono-, di- and triethanolamine salts. The alkyl and acyl groups generally contain from 8 to 18, preferably from 10 to 16 carbon atoms and may be unsaturated. The alkyl ether sulphates, alkyl ether sulphosuccinates, alkyl ether phosphates and alkyl ether carboxylic acids and salts thereof may contain from 1 to 20 ethylene oxide or propylene oxide units per molecule.

Typical anionic cleansing surfactants for use in shampoo compositions of the invention include sodium oleyl succinate, ammonium lauryl sulphosuccinate, sodium lauryl sulphate, sodium lauryl ether sulphate, sodium lauryl ether sulphosuccinate, ammonium lauryl sulphate, ammonium lauryl ether sulphate, sodium dodecylbenzene sulphonate, triethanolamine dodecylbenzene sulphonate, sodium cocoyl isethionate, sodium lauryl isethionate, lauryl ether carboxylic acid and sodium N-lauryl sarcosinate.

Preferred anionic cleansing surfactants are sodium lauryl sulphate, sodium lauryl ether sulphate(n)EO, (where n is from 1 to 3), sodium lauryl ether sulphosuccinate(n)EO, (where n is from 1 to 3), ammonium lauryl sulphate, ammonium lauryl ether sulphate(n)EO, (where n is from 1 to 3), sodium cocoyl isethionate and lauryl ether carboxylic acid (n) EO (where n is from 10 to 20).

Mixtures of any of the foregoing anionic cleansing surfactants may also be suitable.

The total amount of anionic cleansing surfactant preferably ranges from 0.5 to 45%, more preferably from 1 to 30%, and most preferably from 5 to 20% by total weight of the composition.

A preferred additional component in conditioning shampoo compositions according to the invention is silicone oil.

When used, silicone oil is typically present as emulsified droplets having a mean droplet diameter ($D_{3,2}$) of 4 micrometers or less. Preferably the mean droplet diameter ($D_{3,2}$) is 1 micrometer or less, more preferably 0.5 micrometer or less, and most preferably 0.25 micrometer or less.

A suitable method for measuring the mean droplet diameter ($D_{3,2}$) is by laser light scattering using an instrument such as a Malvern Mastersizer.

Preferably the silicone oil is non-volatile, meaning that it has a vapour pressure of less than 1000 Pa at 25° C.

Suitable silicone oils are polydiorganosiloxanes, in particular polydimethylsiloxanes (dimethicones), polydimethyl siloxanes having hydroxyl end groups (dimethiconols), and amino-functional polydimethylsiloxanes (amodimethicones).

Suitable silicones preferably have a molecular weight of greater than 100,000 and more preferably a molecular weight of greater than 250,000.

Suitable silicones preferably have a kinematic viscosity of greater than 50,000 cS ($mm^2 \cdot s^{-1}$) and more preferably a kinematic viscosity of greater than 500,000 cS ($mm^2 \cdot s^{-1}$).

Silicone oil kinematic viscosities as referred to in this specification are measured at 25° C. and can be measured by means of a glass capillary viscometer as set out further in Dow Corning Corporate Test Method CTM004 Jul. 20, 1970.

Suitable silicones for use in compositions of the invention are available as pre-formed silicone emulsions from suppliers such as Dow Corning and GE Silicones. The use of such pre-formed silicone emulsions is preferred for ease of processing and control of silicone particle size. Such pre-formed silicone emulsions will typically additionally comprise a suitable emulsifier, and may be prepared by a chemical emulsification process such as emulsion polymerisation, or by mechanical emulsification using a high shear mixer. Pre-formed silicone emulsions having a Sauter mean droplet diameter ($D_{3,2}$) of less than 0.15 micrometers are generally termed microemulsions.

Examples of suitable pre-formed silicone emulsions include emulsions DC2-1766, DC2-1784, DC-1785, DC-1786, DC-1788, DC-1310, DC-7123 and microemulsions DC2-1865 and DC2-1870, all available from Dow Corning. These are all emulsions/microemulsions of dimethiconol. Also suitable are amodimethicone emulsions such as DC939 (from Dow Corning) and SME253 (from GE Silicones).

Also suitable are silicone emulsions in which certain types of surface active block copolymers of a high molecular weight have been blended with the silicone emulsion droplets, as described for example in WO03/094874.

Mixtures of any of the above described silicone emulsions may also be used.

The total amount of silicone oil in compositions of the invention may suitably range from 0.05 to 10%, particularly from 0.2 to 8%, and especially from 0.5 to 5% by weight of the composition.

A further component that may be used in compositions of the invention is a hydrocarbon oil or ester oil. Like silicone oils, these materials may enhance the conditioning benefits found with compositions of the invention.

Suitable hydrocarbon oils have at least 12 carbon atoms, and include paraffin oil, mineral oil, saturated and unsaturated dodecane, saturated and unsaturated tridecane, saturated and unsaturated tetradecane, saturated and unsaturated pentadecane, saturated and unsaturated hexadecane, and mixtures thereof. Branched-chain isomers of these compounds, as well as of higher chain length hydrocarbons, can also be used. Also suitable are polymeric hydrocarbons of $C_{2-6}$ alkenyl monomers, such as polyisobutylene.

Suitable ester oils have at least 10 carbon atoms, and include esters with hydrocarbyl chains derived from fatty acids or alcohols. Typical ester oils are formula R'COOR in which R' and R independently denote alkyl or alkenyl radicals and the sum of carbon atoms in R' and R is at least 10, preferably at least 20. Di- and trialkyl and alkenyl esters of carboxylic acids can also be used.

Preferred fatty oils are mono-, di- and triglycerides, more specifically the mono-, di-, and tri-esters of glycerol with long chain carboxylic acids such as $C_{1-22}$ carboxylic acids. Examples of such materials include cocoa butter, palm stearin, sunflower oil, soyabean oil and coconut oil.

Mixtures of any of the above described hydrocarbon/ester oils also be used.

The total combined amount of hydrocarbon oil and ester oil in compositions of the invention may suitably range from 0.05 to 10%, particularly from 0.2 to 5%, and especially from 0.5 to 3% by weight of the composition.

A preferred additional component in conditioning shampoo compositions according to the invention is a cationic polymer. Such components may enhance the deliver of conditioning agents and thereby improve the conditioning benefits obtained.

Cationic polymers typically contain cationic nitrogen-containing groups such as quaternary ammonium or protonated amino groups. The cationic protonated amines can be primary, secondary, or tertiary amines (preferably secondary or tertiary). The average molecular weight of the cationic polymer is preferably from 5,000 to 10 million. The cationic polymer preferably has a cationic charge density of from 0.2 meq/gm to 7 meq/gm.

The cationic nitrogen-containing moiety of the cationic polymer is generally present as a substituent on all, or more typically on some, of the repeat units thereof. The cationic polymer may be a homo-polymer or co-polymer of quaternary ammonium or cationic amine-substituted repeat units, optionally in combination with non-cationic repeat units. Non-limiting examples of such polymers are described in the CTFA Cosmetic Ingredient Dictionary, 6th edition, edited by Wenninger, J A and McEwen Jr, G N, (The Cosmetic, Toiletry, and Fragrance Association, 1995). Particularly suitable cationic polymers for use in the composition include polysaccharide polymers, such as cationic cellulose derivatives, cationic starch derivatives, and cationic guars.

Examples of cationic cellulose derivatives are salts of hydroxyethyl cellulose reacted with trimethylammonium substituted epoxide, referred to in the industry (CTFA) as Polyquaternium 10. Further examples of cationic cellulose derivatives are prepared from hydroxyethyl cellulose and lauryldimethylammonium-substituted epoxide and are referred to in the industry (CTFA) as Polyquaternium 24.

Especially preferred cationic polymers are cationic guar gum derivatives, such as guar hydroxypropyltrimonium chloride, specific examples of which include the JAGUAR series commercially available from Rhodia Corp. (e.g., JAGUAR C17 or JAGUAR C13S).

Other suitable cationic polymers include quaternary nitrogen-containing cellulose ethers, examples of which are described in U.S. Pat. No. 3,962,418. Other suitable cationic polymers include derivatives of etherified cellulose, guar and starch, some examples of which are described in U.S. Pat. No. 3,958,581.

Synthetic cationic polymers may also be employed. Examples include co-polymers of vinyl monomers having cationic protonated amine or quaternary ammonium functionality with water soluble spacer repeat units, typically derived from monomers such as acrylamide, methacrylamide, N-alkyl and N,N-dialkyl acrylamides and methacrylamides, alkyl acrylate, allyl methacrylate, vinyl caprolactone, vinyl acetate,/alcohol. Other spacer repeat units may be derived from maleic anhydride, propylene glycol, or ethylene glycol.

Other suitable synthetic cationic polymers include co-polymers of 1-vinyl-2-pyrrolidone and 1-vinyl-3-methylimidazolium salt (e.g., chloride salt), referred to in the industry (CTFA) as Polyquaternium-16; co-polymers of 1-vinyl-2-pyrrolidone and dimethylaminoethyl methacrylate, refereed to in the industry (CTFA) as Polyquaternium-11; cationic diallyl quaternary ammonium-containing polymers, including, for example, dimethyldiallylammonium chloride homo-polymer and co-polymers of acrylamide and dimethyldiallylammonium chloride, referred to in the industry (CTFA) as Polyquaternium 6 and Polyquaternium 7, respectively; and mineral acid salts of amino-alkyl esters of homopolymers and co-polymers of unsaturated carboxylic acids having from 3 to 5 carbon atoms.

The total amount of cationic polymer in the composition is preferably from 0.05% to 2% and more preferably from 0.1 to 0.5% by weight of the composition.

An amphoteric surfactant is a preferred additional ingredient in compositions of the invention. Suitable amphoteric surfactants are betaines, such as those having the general formula $R(CH_3)_2N^+CH_2CO_2^-$, where R is an alkyl or alkylamidoalkyl group, the alkyl group preferably having 10-16 carbon atoms. Particularly suitable betaines are oleyl betaine, caprylamidopropyl betaine, lauramidopropyl betaine, isostearylamidopropyl betaine, and cocoamidopropyl betaine.

Other suitable betaine amphoteric surfactants are sulfobetaines, such as those having the general formula $R'(CH_3)_2N^+CH_2CH(OH)CH_2SO_3^-$, where R' is an alkyl or alkylamidoalkyl group, the alkyl group preferably having 10-16 carbon atoms. Particularly suitable sulfobetaines are laurylamidopropyl hydroxysultaine and cocoamidopropyl hydroxysultaine.

Other suitable amphoteric surfactants are fatty amine oxides, such as lauryldimethylamine oxide.

When included, the total level of amphoteric surfactant is preferably from 0.1% to 20%, more preferably from 1% to 10%, and most preferably from 1% to 5% by weight of the composition.

A Carbomer may be advantageously employed in particular embodiments of the invention. A Carbomer is a homopolymer of acrylic acid crosslinked with an allyl ether of pentaerythritol or an allyl ether of sucrose. Such materials may serve as suspending agents.

When included, the total level of Carbomer is preferably from 0.01% to 10%, more preferably from 0.1% to 5%, and most preferably from 0.25% to 1% by weight of the composition.

Compositions according to the invention may contain other ingredients suitable for use in hair cleansing and conditioning compositions. Such ingredients include but are not limited to: fragrance, suspending agents, amino acids and protein derivatives, viscosity modifiers, preservatives, colourants and pearlisers.

EXAMPLE 1

Table 1 shows two shampoo compositions according to the invention.

TABLE 1

|  | Component | | | |
|---|---|---|---|---|
|  | 1 | | 2 | |
|  | % active in formular | % weight | % active in formular | % weight |
| Sodium laureth sulphate | 12.00 | 17.14 | 12.00 | 17.14 |
| Cocoamidopropyl betaine | 1.60 | 5.33 | 1.60 | 5.33 |
| Guar hydroxypropyl trimonium chloride | 0.20 | 0.20 | 0.20 | 0.20 |
| Glyceryl monostearate | 1.00 | 1.00 | 1.00 | 1.00 |
| Cetyl trimethylammonium chloride | 0.05 | 0.10 | 0.5 | 1.00 |
| Quaternium-90 bentonite | 0.05 | 0.05 | 0.05 | 0.05 |
| Carbomer | 0.40 | 0.40 | 0.40 | 0.40 |
| Ethylene glycol distearate | 0.60 | 4.00 | 0.60 | 4.00 |
| Dimethiconol | 2.00 | 4.00 | 2.00 | 4.00 |
| Fragrance | 0.75 | 0.75 | 0.75 | 0.75 |
| CIT/MIT | 0.0009 | 0.06 | 0.0009 | 0.06 |
| DMDM H | 0.055 | 0.10 | 0.055 | 0.10 |
| EDTA 2Na | 0.10 | 0.10 | 0.10 | 0.10 |
| Sodium chloride | 0.40 | 0.40 | 0.40 | 0.40 |
| Sodium hydroxide | 0.10 | 0.20 | 0.10 | 0.20 |
| Chlorinated water |  | To 100 |  | To 100 |

EXAMPLE 2

Table 2 shows the processing steps required to manufacture composition 1 according to Table 1.

TABLE 2

| Step | Ingredients | Explanation |
|---|---|---|
| 1 | Premix part Glyceryl monostearate Cetyl trimethylammonium chloride Quaternium-90 bentonite | Weigh all material and melt them at 75-80 C. until Glyceryl monostearate and Quaternium-90 bentonite are dissolved together |
| 2 | Sodium laureth sulphate (3%) | Add the premix part into hot SLES which has temperature at 75-80 C. |
| 3 |  | Cool the mixer until 40-45 C. |
| 4 | Main mixer Water Sodium laureth sulphate (9%) | Add the cooled premix part into the main mixer which has water and SLES |
| 5 | Carbomer | Add Carbomer into main mixer |
| 6 | Water EDTA 2Na | Dissolved EDTA 2Na in water and then add into main mixer |
| 7 | Fragrance Guar hydroxypropyl trimonium chloride | Dispersed Guar hydroxypropyl trimonium chloride in Fragrance and then add into the maim mixer |
| 8 | Ethylene glycol distearate | Add Ethylene glycol distearate into the main mixer |
| 9 | Dimethiconol | Add Dimethiconol into the main mixer |
| 10 | Cocoamidopropyl betaine | Add Cocoamidopropyl betaine into the main mixer |
| 11 | CIT/MIT | Add CIT/MIT into the main mixer |
| 12 | DMDM H | Add DMDM H into the main mixer |
| 13 | Sodium hydroxide | Add Sodium hydroxide to adjust pH in spec. |
| 14 | Sodium chloride | Add Sodium Chloride to adjust viscosity in spec. |

EXAMPLE 3

Table 3 shows the processing steps followed to make composition 2 according to Table 1.

TABLE 3

| Step | Ingredients | Explanation |
|---|---|---|
| 1 | Premix part Glyceryl monostearate Cetyl trimethylammonium chloride Quaternium-90 bentonite | Weigh all material and melt them at 75-80 C. until Glyceryl monostearate and Quaternium-90 bentonite are dissolved together |
| 2 | Hot water | Add the premix part into hot water which has temperature at 75-80° C. |
| 3 |  | Cool the mixer until 40-45° C. |
| 4 | Main mixer Water Sodium laureth sulphate | Add the cooled premix part into the main mixer which has water and SLES |
| 5 | Carbomer | Add Carbomer into main mixer |
| 6 | Water EDTA 2Na | Dissolved EDTA 2Na in water and then add into main mixer |
| 7 | Fragrance Guar hydroxypropyl trimonium chloride | Dispersed Guar hydroxypropyl trimonium chloride in Fragrance and then add into the maim mixer |
| 8 | Ethylene glycol distearate | Add Ethylene glycol distearate into the main mixer |
| 9 | Dimethiconol | Add Dimethiconol into the main mixer |
| 10 | Cocoamidopropyl betaine | Add Cocoamidopropyl betaine into the main mixer |
| 11 | CIT/MIT | Add CIT/MIT into the main mixer |

TABLE 3-continued

| Step | Ingredients | Explanation |
|---|---|---|
| 12 | DMDM H | Add DMDM H into the main mixer |
| 13 | Sodium hydroxide | Add Sodium hydroxide to adjust pH in spec. |
| 14 | Sodium chloride | Add Sodium Chloride to adjust viscosity in spec. |

EXAMPLE 4

Table 4 shows the transition temperatures of compositions according to table 1 with various different fatty materials. The results show the transition temperature by DSC scanning and thus the stability of the compositions at elevated temperatures. The table shows that GMS provides a compositions with a higher temperature stability than fatty alcohol or fatty acid.

TABLE 4

| Fatty compounds | Melting point | Transition temperature by DSC scanning |
|---|---|---|
| Fatty alcohol | | |
| Cetyl alcohol (C16H34O) | 55-60° C. | Form gel at 30-40° C. |
| Behenyl alcohol (C22H46O) | 65-73° C. | Form gel at 44-55° C. |
| Fatty acid | | |
| Palmitic acid (C16H32O2) | 61-64° C. | Form gel at 30-40° C. |
| Fatty ester | | |
| Glyceryl Stearate (GMS) | 58-61° C. | Form gel at 65-68° C. |

The invention claimed is:

1. Aqueous conditioning shampoo comprising cleansing surfactant and a conditioning gel network, wherein said gel network comprises 0.05 to 10% silicone oil and comprises $L_\beta$ lamellar phase dispersion at 25° C.;
  wherein said gel network additionally comprises a hydrophobically modified bentonite clay having melting point above 75° C. and a quaternary ammonium compound having at least one carbon chain of length $C_{12}$-$C_{30}$;
  wherein said gel network further comprises glyceryl monostearate to enhance stability of said network comprising said clay and said quaternary ammonium compared to a network in which fatty alcohol or fatty acid are used to provide temperature stability instead of glyceryl monostearate;
  wherein a premix of said gel network is formed by melting the glyceryl monostearate in water and subsequently adding said bentonite clay and said quaternary ammonium to form a dispersion of liquid crystalline phase droplets.

* * * * *